(12) United States Patent
Pomerantz et al.

(10) Patent No.: US 9,416,656 B2
(45) Date of Patent: Aug. 16, 2016

(54) ASSESSING RESERVOIR CONNECTIVITY IN HYDROCARBON RESERVOIRS (71) Applicant: Schlumberger Technology Corporation, Sugar Land, TX (US)

(72) Inventors: Andrew E. Pomerantz, Lexington, MA (US); Youxiang Zuo, Burnaby (CA); Oliver C. Mullins, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 25 days.

(21) Appl. No.: 14/406,516

(22) PCT Filed: Mar. 7, 2013

(86) PCT No.: PCT/US2013/029549
§ 371 (c)(1),
(2) Date: Dec. 8, 2014

(87) PCT Pub. No.: WO2013/184190
PCT Pub. Date: Dec. 12, 2013

(65) Prior Publication Data
US 2015/0136962 A1 May 21, 2015

Related U.S. Application Data

(60) Provisional application No. 61/657,070, filed on Jun. 8, 2012.

(51) Int. Cl.
*E21B 49/08* (2006.01)
*E21B 47/00* (2012.01)
(Continued)

(52) U.S. Cl.
CPC .............. *E21B 49/088* (2013.01); *E21B 47/00* (2013.01); *E21B 47/10* (2013.01); *E21B 49/00* (2013.01); *E21B 49/02* (2013.01); *E21B 49/082* (2013.01); *G01N 21/64* (2013.01); *G01N 2201/12* (2013.01)

(58) Field of Classification Search
CPC ....... E21B 49/088; E21B 47/00; E21B 49/00; E21B 49/02; G01N 21/64
See application file for complete search history.

(56) References Cited

U.S. PATENT DOCUMENTS

| 4,994,671 A | 2/1991 | Safinya et al. |
| 7,530,265 B2 | 5/2009 | DiFoggio |

(Continued)

FOREIGN PATENT DOCUMENTS

| WO | 2009093105 A1 | 7/2009 |
| WO | 2009138911 A2 | 11/2009 |

(Continued)

OTHER PUBLICATIONS

International Search Report for International Application No. PCT/US2013/029549 dated Jun. 18, 2013.

(Continued)

*Primary Examiner* — Christine Sung
(74) *Attorney, Agent, or Firm* — David G. Matthews; Cathy Hewitt (57) ABSTRACT

A method is disclosed for assessing connectivity between sections in a hydrocarbon reservoir. Samples of hydrocarbons are collected over different depths in at least one wellbore. Fluorescence intensity determines the actual heavy end concentrations of hydrocarbons for the corresponding different depths. Estimated heavy end concentrations of hydrocarbons for corresponding different depths are determined and the actual heavy end concentrations of hydrocarbons are compared with the estimated heavy end concentrations to assess connectivity between sections of the hydrocarbon reservoir.

18 Claims, 5 Drawing Sheets

(51) Int. Cl.
*E21B 49/00* (2006.01)
*E21B 49/02* (2006.01)
*G01N 21/64* (2006.01)
*E21B 47/10* (2012.01)

(56) References Cited

U.S. PATENT DOCUMENTS

| | | |
|---|---|---|
| 7,822,554 B2 | 10/2010 | Zuo et al. |
| 7,920,970 B2 | 4/2011 | Zuo et al. |
| 8,271,248 B2 | 9/2012 | Pomerantz et al. |
| 2008/0037006 A1* | 2/2008 | Canas Triana ........ E21B 47/102 356/73 |
| 2009/0248310 A1 | 10/2009 | Zuo et al. |
| 2009/0312997 A1 | 12/2009 | Freed et al. |
| 2010/0228485 A1 | 9/2010 | Betancourt et al. |
| 2010/0235154 A1* | 9/2010 | Meurer .................. G01V 11/00 703/10 |
| 2011/0088895 A1 | 4/2011 | Pop et al. |
| 2012/0053838 A1 | 3/2012 | Andrews et al. |
| 2013/0273661 A1 | 10/2013 | Pomerantz |
| 2014/0200810 A1* | 7/2014 | Zuo ........................ E21B 49/10 702/13 |
| 2014/0202237 A1* | 7/2014 | Pomerantz ............ E21B 49/088 73/61.43 |
| 2014/0208826 A1* | 7/2014 | Larter .................... E21B 49/06 73/23.41 |

FOREIGN PATENT DOCUMENTS

| | | | |
|---|---|---|---|
| WO | 2011007268 A1 | 1/2011 | |
| WO | 2011030243 A1 | 3/2011 | |
| WO | 2011138700 A2 | 11/2011 | |
| WO | 2012042397 A2 | 4/2012 | |
| WO | WO 2012042397 A2 * | 4/2012 | .............. E21B 49/10 |
| WO | 2013106736 A1 | 7/2013 | |
| WO | 2013109716 A1 | 7/2013 | |
| WO | 2013184190 A1 | 12/2013 | |

OTHER PUBLICATIONS

Juyal, et al. "Analysis and Identification of Biomarkers and Origin of Color in a Bright Blue Crude Oil," Energy Fuels, 2011, 25, pp. 172-182.

Communication pursuant to Article 94(3) EPC for European Application No. 13800589.7 dated Apr. 4, 2016.

Supplementary European Search Report for European Application No. 13800589.7 dated Feb. 24, 2016.

* cited by examiner

ASSESSING RESERVOIR CONNECTIVITY IN HYDROCARBON RESERVOIRS

BACKGROUND

Reservoir connectivity analysis determines whether reservoir fluids flow from one reservoir section to another reservoir section and where to drill a wellbore. Reservoir connectivity may be assessed by collecting and analyzing oil samples from a wellbore using Downhole Fluid Analysis (DFA), including optical spectroscopy to determine heavy end concentration at different depths in the wellbore and comparing to a Flory-Huggins-Zuo Equation of State (FHZ EOS) oils. This analysis relies on the interpretation of the optical absorption in the visible or near infrared region (referred to as "color") and is related to the relative content of asphaltenes or colored resins in the oil. It is difficult, however, to quantify the asphaltene content in some oils. Some systems measure relative asphaltene content using color and heavy oil fluorescence, both of which are appropriate for oils with a high concentration of heavy ends. These methods may not be viable for oils with a low concentration of heavy ends, such as gas condensates.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method assesses connectivity between sections in a hydrocarbon reservoir traversed by a wellbore. A plurality of hydrocarbons are collected over corresponding depths within at least one wellbore. Fluorescence intensity is used to determine a plurality of actual heavy end concentrations of hydrocarbons for the corresponding different depths based upon the plurality of hydrocarbon samples. A plurality of estimated heavy end concentrations of hydrocarbons for the corresponding depths are determined. The plurality of actual heavy end concentrations of the hydrocarbons are compared with the plurality of estimated heavy end concentrations of hydrocarbons to assess connectivity between adjacent sections of the hydrocarbon reservoir.

In one example the hydrocarbon is formed as a gas condensate, wet gas or volatile oil. In another example the hydrocarbon is formed as a fluid containing <1 wt % asphaltene. The hydrocarbon may also be formed as a fluid with <0.1 optical density (OD) absorption in the visible or near-infrared spectral regions. In another example the hydrocarbon is formed as fluid having heavy ends existing as isolated molecules. In yet another example, the hydrocarbon is formed as a fluid having a fluorescence proportional to the heavy end content.

In an example, a plurality of estimated heavy end concentrations have a gradient over the depth of the wellbore indicative of connectivity between sections of the hydrocarbon reservoir. The plurality of hydrocarbon samples may be collected using a downhole tool within the wellbore. In another example, the plurality of estimated heavy end concentrations are determined using a Flory-Huggins-Zuo Equation of State (FHZ EOS) model. The heavy end concentrations may be based upon the concentrations of aromatics and resins, which may have a chemical composition similar to the molecule perylene.

A system of assessing connectivity between sections in a hydrocarbon reservoir traversed by at least one wellbore includes at least one tool to collect a plurality of hydrocarbon samples over corresponding depths within the at least one wellbore. Fluorescence intensity is used to determine the actual heavy end concentrations of hydrocarbons. A processor cooperates with the at least one tool and determines the estimated heavy end concentrations, and compares the plurality of actual heavy end concentrations of hydrocarbons with the estimated heavy end concentrations of hydrocarbons to assess connectivity between sections of the hydrocarbon reservoir.

A non-transitory computer readable medium is also disclosed and is executable on a processor to perform steps to assess connectivity between the sections in a hydrocarbon reservoir and traversed by a wellbore and for which fluorescence intensity has been used to determine the actual heavy end concentrations of gas condensates for the corresponding different depths. It compares actual heavy end concentrations of hydrocarbons with the estimated heavy end concentrations.

DETAILED DESCRIPTION

The present description is made with reference to the accompanying drawings, in which example embodiments are shown. However, many different embodiments may be used, and thus the description should not be construed as limited to the embodiments set forth herein. Rather, these embodiments are provided so that this disclosure will be thorough and complete. Like numbers refer to like elements throughout.

Figure 1A:
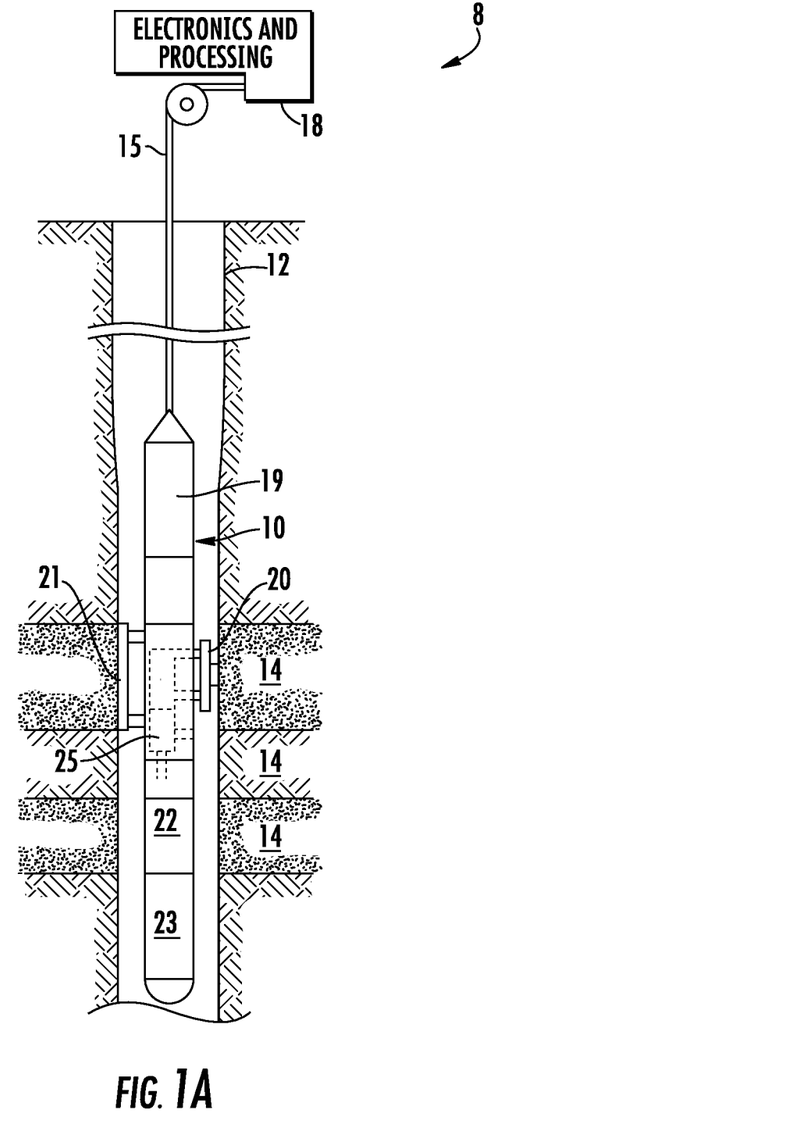
FIG. 1A is a schematic diagram of a petroleum reservoir fluid analysis tool that may be used with the methodology in accordance with a non-limiting embodiment.
Figure 1B:
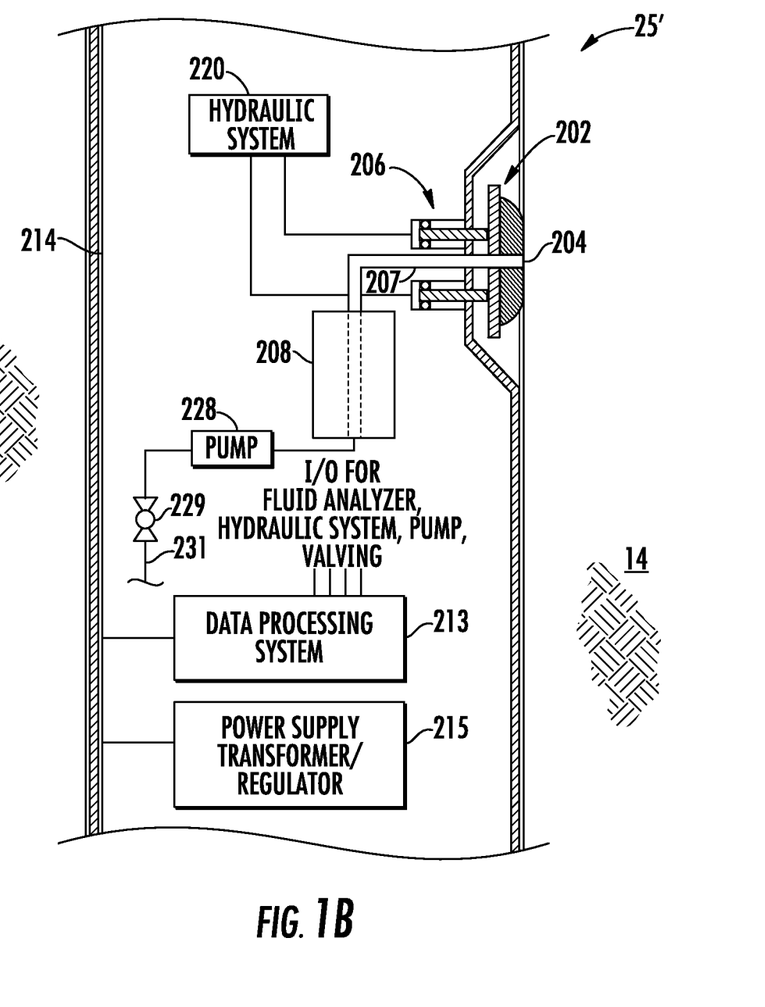
FIG. 1B is a schematic diagram of a fluid analysis module suitable for use with the tool of FIG. 1A.

Referring now to FIGS. 1A and 1B, there is illustrated a tool for controlling a reservoir downhole fluid analysis (DFA) module and in FIG. 1B, an example embodiment of the fluid analysis module of FIG. 1A that includes various probes including a probe to measure fluorescence data and enable assessment of reservoir connectivity in gas condensates using the FHZ EOS. Substantial details of the FHZ EOS are described in commonly assigned international patent application publication no. WO 2012/042397 based on U.S. provisional patent application Ser. No. 61/387,066 and commonly assigned U.S. provisional patent application Ser. No. 61/587,846.

Application of the FHZ EOS is described below relative to the subject matter of measuring heavy end gas concentrations of hydrocarbons, such as gas condensates, to determine reservoir connectivity. A system that measures asphaltene content using spectroscopy is disclosed in commonly assigned U.S. patent application Ser. No. 13/446,975, and another system using fluorescence is disclosed in international patent application no. PCT/US13/21274, based on U.S. provisional patent application Ser. No. 61/585,934. The system and method as described below may be used in one or more boreholes intersecting a common formation. This analysis is not restricted to a single borehole. Lateral connectivity is often analyzed and a single well or multi-well approach may be used.

Gas condensates exhibit little color, indicating that the relative concentration of heavy ends cannot be determined by optical spectroscopy. Application of the FHZ EOS to assess reservoir connectivity relies on measurements of relative concentration of the heavy ends. In accordance with a non-limiting example, hydrocarbons such as gas condensates are measured using fluorescence data to enable assessment of the reservoir connectivity in gas condensates using the FHZ EOS.

In one example the hydrocarbon is formed as a gas condensate and in another example as a wet gas having a small amount of liquid present, such a ranging from a humid gas that is gas saturated with liquid vapor to a multi-phase flow with a 90% volume of gas in a non-limiting example. In another example the hydrocarbon is formed as a volatile oil or a fluid containing <1 wt % asphaltene. The hydrocarbon may also be formed with <0.1 optical density (OD) absorption in the visible or near-infrared spectral regions. A hydrocarbon may also be formed as a fluid having heavy ends exist as isolated molecules. The hydrocarbon may also be formed as a fluid having fluorescence that is proportional to the heavy end content.

FIG. 1A illustrates a petroleum reservoir analysis system 8 that can be used in accordance with a non-limiting example to assess reservoir connectivity. The system 8 includes a borehole tool 10 suspended in the borehole 12 from the lower end of a typical multiconductor cable 15 that is spooled in a usual fashion on a suitable winch on the formation surface. The cable 15 is electrically coupled to a control system 18 on the formation surface and includes electronics and processing circuitry for processing the tool. The borehole tool 10 includes an elongated body 19 which carries a selectively extendable fluid admitting assembly 20 and a selectively extendable tool anchoring member 21 which are respectively arranged on opposite sides of the tool body. The fluid admitting assembly 20 is equipped for selectively sealing off or isolating selected portions of the wall of the borehole 12 such that fluid communication with the adjacent earth formation 14 is established.

The fluid admitting assembly 20 and borehole tool 10 include a flowline leading to a fluid analysis module 25. The formation fluid obtained by the fluid admitting assembly 20 flows through the flowline and through the fluid analysis module 25. The fluid may thereafter be expelled through a port or it may be sent to one or more fluid collecting chambers 22 and 23 that may receive and retain the fluids obtained from the formation. With the fluid admitting assembly 20 sealingly engaging the formation 14, a short rapid pressure drop can be used to break the mudcake seal. The first fluid drawn into the tool may be highly contaminated with mud filtrate. As the tool continues to draw fluid from the formation 14, the area near the fluid admitting assembly 20 cleans up and reservoir fluid becomes the dominant constituent. The time required for cleanup depends upon many parameters, including formation permeability, fluid viscosity, the pressure differences between the borehole and the formation, and overbalanced pressure difference and its duration during drilling. Increasing the pump rate can shorten the clean-up time, but the rate is controlled carefully to preserve formation pressure conditions.

The fluid analysis module 25 includes components to measure the temperature and pressure of the fluid in the flowline. The module may work in conjunction with a circuit and apparatus that measures the fluorescence intensity in different samples of gas condensates that are collected at different depths within the wellbore. Reference is made to the incorporated by reference international patent application PCT/US 13/21274 that discloses heavy oil fluorescence to measure the asphaltene content of heavy oil and includes various sensors and modules that measure the fluorescence of gas condensates. The fluid analysis module 25 also derives properties that characterize the formation fluid sample at the flowline pressure and temperature.

In one embodiment, the fluid analysis module 25 measures absorption spectra and translates such measurements into concentrations of several alkane components and groups in the fluid sample. In an illustrative embodiment, the fluid analysis module 25 provides measurements of the concentrations (e.g., weight percentages) of carbon dioxide ($CO_2$), methane ($CH_4$), ethane ($C_2H_6$), the C3-C5 alkane group, the lump of hexane and heavier alkane components (C6+), and asphaltene content. The fluid analysis module 25 measures live fluid density ($\rho$) at the flowline temperature and pressure, live fluid viscosity ($\mu$) at flowline temperature and pressure (in cP), formation pressure, and formation temperature.

Control of the fluid admitting assembly 20 and fluid analysis module 25, and the flow path to the collecting chambers 22, 23 are maintained by the control system 18. As will be appreciated by those skilled in the art, the fluid analysis module 25 and the surface-located electrical control system 18 include data processing functionality (e.g., one or more microprocessors, associated memory, and other hardware and/or software) to implement the methodology as described herein. The electrical control system 18 may also be realized by a distributed data processing system. The data measured by the borehole tool 10 is communicated (for example, in real time) over a communication link, e.g., a satellite link, to a remote location for data analysis, which can be carried out on a workstation or other suitable data processing system, e.g., a computer cluster or computing grid.

Formation fluids sampled by the borehole tool 10 may be contaminated with the mud filtrate of a drilling fluid that seeps into the formation 14 during the drilling process. In some examples, formation fluids are withdrawn from the formation 14 and pumped into the borehole or into a large waste chamber in the borehole tool 10 until the fluid being withdrawn becomes sufficiently clean. In a clean sample, the concentration of mud filtrate in the sample fluid is acceptably low so that the fluid substantially represents native (i.e., naturally occurring) formation fluids. In the illustrated example, the borehole tool 10 is provided with fluid collecting chambers 22 and 23 to store collected fluid samples.

The system 8 of FIG. 1A makes in situ determinations regarding hydrocarbon bearing geological formations by downhole sampling of reservoir fluid at one or more measurement stations within the borehole 12 and conducts downhole fluid analysis (DFA) of one or more reservoir fluid samples for each measurement station (including compositional analysis such as estimating concentrations of a plurality of compositional components of a given sample and other fluid properties). In accordance with a non-limiting example, the samples of gas condensates are collected from different depths. The downhole fluid analysis may be compared to an equation of state (EOS) model of the thermodynamic behavior of the fluid to characterize the reservoir fluid at different locations within the reservoir and determine fluid production parameters, transport properties, and other commercially useful indicators of the reservoir.

For example, the EOS model may provide a phase envelope that may be used to vary interactively the rate at which samples are collected and avoid entering the two-phase region. In another example, the EOS may assess production methodologies for the reservoir. Such properties may include density, viscosity, and volume of gas formed from a liquid after expansion to a specified temperature and pressure. The characterization of the fluid sample with respect to its thermodynamic model may also be used as a benchmark to determine the validity of the obtained sample, whether to retain the sample, and/or whether to obtain another sample at the location of interest. More particularly, based on the thermodynamic model and information regarding formation pressures, sampling pressures, and formation temperatures, if it is determined that the fluid sample was obtained near or below the bubble point of the sample, a decision may be made to jettison the sample and/or to obtain a sample at a slower rate (i.e., a smaller pressure drop) so that gas will not evolve out of the sample. Because knowledge of the exact dew point of a retrograde gas condensate in a formation may be desirable, a decision may be made, when conditions allow, to vary the pressure drawdown in an attempt to observe the liquid condensation and thus establish the actual saturation pressure.

FIG. 1B illustrates an embodiment of the fluid analysis module 25 of FIG. 1A (labeled 25'), including a probe 202 having a port 204 to admit formation fluid therein. A hydraulic extending mechanism 206 may be driven by a hydraulic system 220 to extend the probe 202 to sealingly engage the formation 14. In other implementations, more than one probe may be used or inflatable packers may replace the probe(s) and function to establish fluid connections with the formation and sample fluid samples.

An example probe 202 is the Quicksilver Probe developed by Schlumberger Technology Corporation of Sugar Land, Tex., USA. The Quicksilver Probe divides the fluid flow from the reservoir into two concentric zones, i.e., a central zone isolated from a guard zone about the perimeter of the central zone. The two zones are connected to separate flowlines with independent pumps. The pumps can be run at different rates to exploit filtrate/fluid viscosity contrast and permeability anistrotropy of the reservoir. Higher intake velocity in the guard zone directs contaminated fluid into the guard zone flowline, while clean fluid is drawn into the central zone. Fluid analyzers analyze the fluid in each flowline to determine the composition of the fluid in the respective flowlines. The pump rates can be adjusted based on such compositional analysis to achieve and maintain desired fluid contamination levels. The operation of the Quicksilver Probe efficiently separates contaminated fluid from cleaner fluid early in the fluid extraction process, which results in obtaining clean fluid in much less time compared to traditional formation testing tools.

The fluid analysis module 25' includes a flowline 207 that carries formation fluid from the port 204 through a fluid analyzer 208. The fluid analyzer 208 may include a light source that directs light to a sapphire prism disposed adjacent the flowline fluid flow. The reflection of such light is analyzed by a gas refractometer and dual fluoroscene detectors. The gas refractometer qualitatively identifies the fluid phase in the flowline. The dual fluoroscene detectors detect free gas bubbles and retrograde liquid dropout to accurately detect single phase fluid flow in the flowline 207. Fluid type is also identified. The resulting phase information can be used to define the difference between retrograde condensates and volatile oils, which can have similar gas-oil ratios (GORs) and live-oil densities. It can also be used to monitor phase separation in real time and ensure single phase sampling. The fluid analyzer 208 also includes dual spectrometers—a filter array spectrometer and a grating-type spectrometer. The fluid analyzer 208 or other associated modules also include apparatus to measure the fluorescence intensity in samples of gas condensates at different depths within the wellbore.

The filter array spectrometer of the analyzer 208 includes a broadband light source providing broadband light that passes along optical guides and through an optical chamber in the flowline to an array of optical density detectors that are designed to detect narrow frequency bands (commonly referred to as channels) in the visible and near-infrared spectra as described in U.S. Pat. No. 4,994,671. The filter array spectrometer also employs optical filters that provide for identification of the color (also referred to as "optical density" or "OD") of the fluid in the flowline. Such color measurements support fluid identification, determination of asphaltene content and pH measurement. This grating type spectrometer of the fluid analyzer 208 is designed to detect channels in the near-infrared spectra (between 1600-1800 nm) where reservoir fluid has absorption characteristics that reflect molecular structure.

The fluid analyzer 208 also includes a pressure sensor for measuring pressure of the formation fluid in the flowline 207, a temperature sensor for measuring temperature of the formation fluid in the flowline 207, and a density sensor for measuring live fluid density of the fluid in the flowline 207. In addition to density, the density sensor can also provide a measurement of live fluid viscosity from the quality factor of oscillation frequency. In one embodiment, the fluid analyzer 208 is the Insitu Fluid Analyzer commercially available from Schlumberger Technology Corporation. The flowline sensors of the fluid analyzer 208 may be replaced or supplemented with other types of suitable measurement sensors (e.g., NMR sensors, capacitance sensors, etc.). Pressure sensor(s) and/or temperature sensor(s) for measuring pressure and temperature of fluid drawn into the flowline 207 can also be part of the probe 202.

A pump 228 is fluidly coupled to the flowline 207 and is controlled to draw formation fluid into the flowline 207 and supply formation fluid to the fluid collecting chambers 22 and 23 (FIG. 1A) via valve 229 and flowpath 231 (FIG. 1B).

The fluid analysis module 25' includes a data processing system 213 that receives and transmits control and data signals to the other components of the module 25' for controlling operations of the module 25'. The data processing system 213 also communicates with the fluid analyzer 208 for receiving, storing, and processing the measurement data generated therein. In one embodiment, the data processing system 213 processes the measurement data output by the fluid analyzer 208 to derive and store measurements of the hydrocarbon composition of fluid samples analyzed insitu by the fluid analyzer 208, including: flowline temperature; flowline pressure; live fluid density ($\rho$) at the flowline temperature and pressure; live fluid viscosity ($\mu$) at flowline temperature and pressure; concentrations (e.g., weight percentages) of carbon dioxide ($CO_2$), methane ($CH_4$), ethane ($C_2H_6$), the C3-C5 alkane group, the lump of hexane and heavier alkane components (C6+), and asphaltene content; gas/oil ratio (GOR); and other parameters (such as API gravity, oil formation volume factor ($B_0$), etc.).

Flowline temperature and pressure is measured by the temperature sensor and pressure sensor, respectively, of the fluid analyzer 208 (and/or probe 202). In one embodiment, the output of the temperature sensor(s) and pressure sensor(s) are monitored continuously before, during, and after sample acquisition to derive the temperature and pressure of the fluid in the flowline 207. Formation pressure can be measured by the pressure sensor of the fluid analyzer 208 in conjunction with the downhole fluid sampling and analysis at a particular measurement station after buildup of the flowline to formation pressure.

The GOR is determined by measuring the quantity of methane and liquid components of crude oil using near infrared absorption peaks. The ratio of the methane peak to the oil peak on a single phase live crude oil is directly related to GOR. The fluid analysis module 25' can also detect and/or measure other fluid properties of a given live oil sample, including retrograde dew formation, asphaltene precipitation, and/or gas evolution.

The fluid analysis module 25' also includes a tool bus 214 that communicates data signals and control signals between the data processing system 213 and the surface-located control system 18 of FIG. 1A. The tool bus 214 can also carry electric power supply signals generated by a surface-located power source for supply to the fluid analysis module 25', and the module 25' can include a power supply transformer/regulator 215 for transforming the electric power supply signals supplied via the tool bus 214 to appropriate levels suitable for use by the electrical components of the module 25'.

Although the components of FIG. 1B are shown and described above as being communicatively coupled and arranged in a particular configuration, persons of ordinary skill in the art will appreciate that the components of the fluid analysis module 25' can be communicatively coupled and/or arranged differently than depicted in FIG. 1B without departing from the scope of the present disclosure. In addition, the example methods, apparatus, and systems described herein are not limited to a particular conveyance type but, instead, may be implemented in connection with different conveyance types including, for example, coiled tubing, wireline, wired-drill-pipe, and/or other conveyance mechanisms known in the industry.

In accordance with the present disclosure, the system of FIGS. 1A and 1B can operate using the methodology shown in the flowchart 300 of FIG. 2 to assess connectivity based on downhole fluid analysis (DFA) of samples of reservoir fluid and more particularly the gas condensates as explained in detail below. As will be appreciated by those skilled in the art, the surface-located electrical control system 18 and the fluid analysis module 25 of the borehole tool 10 each include data processing functionality (e.g., one or more microprocessors, associated memory, and other hardware and/or software) that cooperate to implement the method as described herein. The electrical control system 18 can also be realized by a distributed data processing system or workstation or other suitable data processing system (such as a computer cluster or computing grid).

There now follows greater details of the method used to assess reservoir connectivity for gas condensate reservoirs. A short description of the structure and analysis methodology of asphaltenes is first described in order to understand better the process as described when FHZ EOS is applied to heavy end gas condensates.

Asphaltenes are a solubility class of crude oil that are soluble in the aromatic solvent but insoluble in the n-alkanes. The asphaltenes are solids that precipitate when an excess of n-heptane or pentane is added to crude oil. Asphaltene molecules are polar with relatively high molecular weights (about 700 to about 1,000 g/mol) and a density of about 1.2 g/cc and can precipitate from crude oil current production. During oil production, asphaltenes often are destabilized and precipitate because of changes in temperature, pressure and/or the chemical composition of the crude.

Reservoir fluids may be classified using nanoscience to measure the compositional gradients in the oil columns. Compartmentalization, connectivity, fluid gradients and viscosity may be materially affected by small amounts of asphaltene. The oil viscosity depends on the asphaltene content. The magnitude of fluid gradients depends on the aggregate structures of asphaltenes, which depends on the asphaltene content among other variables. Measurements of asphaltene gradients are indicative of connectivity and compartmentalization, but small amounts of asphaltene do not cause a reservoir to be compartmentalized. Downhole fluid sampling analysis can enable accurate measurement of the asphaltene content variation across the oil column. The asphaltene content and distribution is gathered using a combination of sensors and the measured gradients and coloration, fluid density, gas/oil ratio (GOR), hydrocarbon composition, fluorescence intensity and viscosity are measured in-situ. Fluid property measurements are performed downhole and transmitted to the surface in real time as IFA data and coupled with the asphaltene Equation of State (EOS) models. As a result, it is possible to determine reservoir complexity such as the flow barriers and fluid distributions and compartmentalization. Because asphaltenes are solid, they are treated with a colloidal EOS, such as the Flory-Huggins-Zuo (FHZ) EOS. The downhole fluid analysis data is processed with the FHZ EOS as applied and a determination made if asphaltene is distributed in thermodynamic equilibrium across a reservoir.

Figure 2:
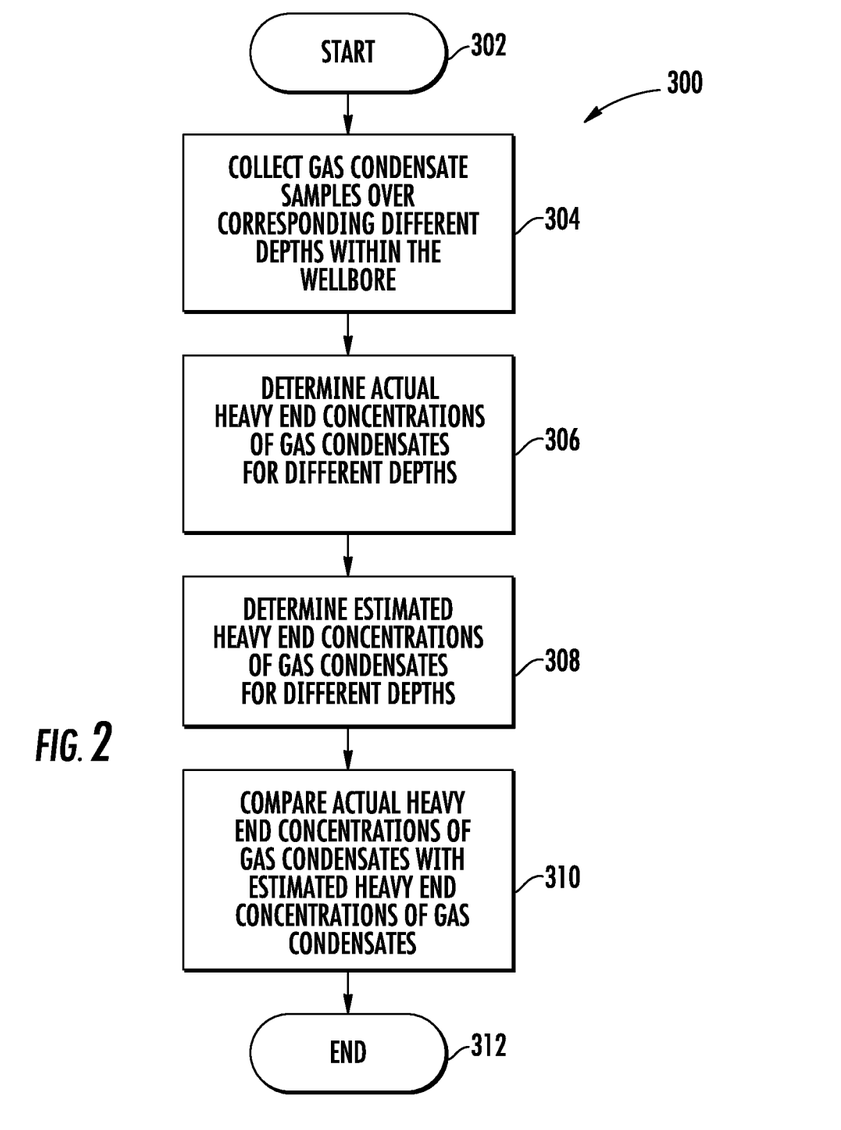
FIG. 2 is a flowchart showing a workflow for assessing connectivity in accordance with a non-limiting embodiment.

FIG. 2 is a high-level flowchart 300 showing an example method that assesses connectivity in gas condensate reservoirs. The method assesses connectivity between adjacent sections in a hydrocarbon reservoir traversed by a wellbore. Gas condensates exhibit little color and the relative concentration of heavy ends cannot be determined by optical spectroscopy. The conventional application of the Flory-Huggins-Zuo Equation of State (FHZ EOS) to assess the reservoir connectivity relies on measurements of relative concentration of the heavy end. As a result the FHZ EOS had not been applied in gas condensates because the required measurements were not available.

The flowchart 300 shown in FIG. 2 is a high-level flow diagram of a method that assesses connectivity between adjacent sections in a hydrocarbon reservoir traversed by a wellbore. After the start (block 302), a plurality of gas condensate samples are collected over corresponding different depths within the wellbore (block 304). The fluorescence intensity is used to determine a plurality of actual heavy end concentrations of gas condensates for the corresponding different depths based upon the plurality of gas condensate samples (block 306). A plurality of estimated heavy end concentrations of gas condensates for the corresponding different depths are determined (block 308). The plurality of actual heavy end concentrations of gas condensates are compared with the plurality of estimated heavy end concentrations of gas condensates to assess connectivity between adjacent sections of the hydrocarbon reservoir (block 310). The method ends at block 312.

In one example, the plurality of estimated heavy end concentrations have a gradient over the depth of the wellbore indicative of connectivity between adjacent sections of the hydrocarbon reservoir. As noted above, the FHZ EOS model is used to determine the plurality of estimated heavy end concentrations, which can be based upon concentrations of aromatics and resins.

As noted above, the system of assessing connectivity includes the at least one tool that collects the plurality of gas condensate samples and uses the fluorescence intensity to determine the plurality of actual heavy end concentrations of gas condensates for the corresponding different depths based upon the plurality of gas condensate samples. The processor shown in FIG. 1A cooperates with the a tool, such as that described above with respect to FIGS. 1A and 1B, and determines the plurality of estimated heavy end concentrations of gas condensates for the corresponding different depths and makes the comparison.

A non-transitory computer readable medium corresponds in one example to the electronics and processing and is executable on a processor to perform the steps to assess the connectivity between adjacent sections in a hydrocarbon reservoir traversed by the wellbore from which a plurality of gas condensate samples have been collected over corresponding different depths within the wellbore. The fluorescence intensity has been used to determine a plurality of actual heavy end concentrations of gas condensates for the corresponding different depths based upon the plurality of gas condensate samples. The different steps are performed by determining the plurality of estimated heavy end concentrations of gas condensates for the corresponding different depths and comparing the plurality of actual heavy end concentrations of gas condensates with the plurality of estimated heavy end concentrations of gas condensates to assess connectivity between adjacent sections of the hydrocarbon reservoir.

There now follows further details of the methodology in accordance with a non-limiting example. For example, the gas condensate samples may be collected at multiple depths using a MDT™ modular formation dynamics tester such as available from Schlumberger Technology Corporation of Sugarland, Tex., USA. This tester measures the reservoir pressure and collects representative fluid samples from multiple layers while providing permeability and anisotropy data through different interval pressure transient tests. This type of MDT tester may include basic components of an Electronic Power Module (MRPC), Hydraulic Power Module (MRHY), Single Probe Module (MRPS), and Modular Sample Chambers (MRSC). The fluorescence of these samples is measured using Downhole Fluid Analysis (DFA) in order to determine a plurality of actual heavy end concentrations of gas condensates for the corresponding different depths based on the plurality of gas condensate samples. The downhole fluid sampling as described above may be accomplished in one example using a wireline formation testing and sampling tool (WFT) to acquire samples at different depths with good vertical resolution. Any contamination may be corrected using an Oil-based Contamination Monitor (OCM) that is also available from Schlumberger Technology Corporation.

In one example, the OCM technique uses an optical device to monitor the build-up of color during sampling and provide real-time analysis of sample contamination. It processes the data to predict how long it will take to achieve an acceptably low level of contamination. For example, the reservoir fluid replaces the filtrate in a flow line and the Optical Density (OD) of a methane signal increases in proportion to the methane content of the oil in a non-limiting example. Methane detection is used for condensates and for lightly colored crude oils. In these fluids, the color build-up is difficult to detect but the high methane content makes possible a reliable methane-based OCM algorithm. The methane content may also be used to determine the gas/oil ratio (GOR) of the sample. For example, when a formation fluid sample is taken from a well that is drilled with the Oil-Based Mud (OBM), sample contamination by the OBM filtrate may affect the accurate measurement of the sample PVT properties. The in-situ sample OBM contamination may be predicted in real time by the Live Fluid Analyzer (LFA).

After a correction is made for the contamination, the florescence intensity is interpreted proportional to the heavy end concentration of the condensates relative to the other condensates in the field. Gas condensates contain mainly light ends with little to no asphaltenes. The majority of those compounds are saturated hydrocarbons, which do not fluoresce. The condensates have some compounds that contain aromatic carbon as aromatics or resins in the SARA classification and fluoresce. These are the similar compounds that lead to fluorescence in black oils, which also contain asphaltenes, which predominantly serve to quench, i.e., prevent fluorescence. In black oils, an increase in asphaltenes results in more quenching and less fluorescence. Gas condensates do not contain fluorescence quenchers, however, and in gas condensates an increase in the heavy ends, such as the aromatics and resins, results in more fluorophores and therefore more fluorescence. The fluorescence of light oils is modeled as linearly proportional to the concentration of heavy ends because there are no quenchers to disrupt the linearity.

Crude oil may be divided into four classes: saturates, aromatics, resins, and asphaltenes. Saturates generally do not participate in fluorescence. Aromatics and resins are fluorophores but not quenchers, in that they absorb incident photons and emit fluorescent photons, but they do not react with themselves to quench. Asphaltenes are quenchers but not fluorophores, in that they do not fluoresce at concentrations found in most crude oil, but they quench fluorescence from resins and aromatics.

Figure 3:
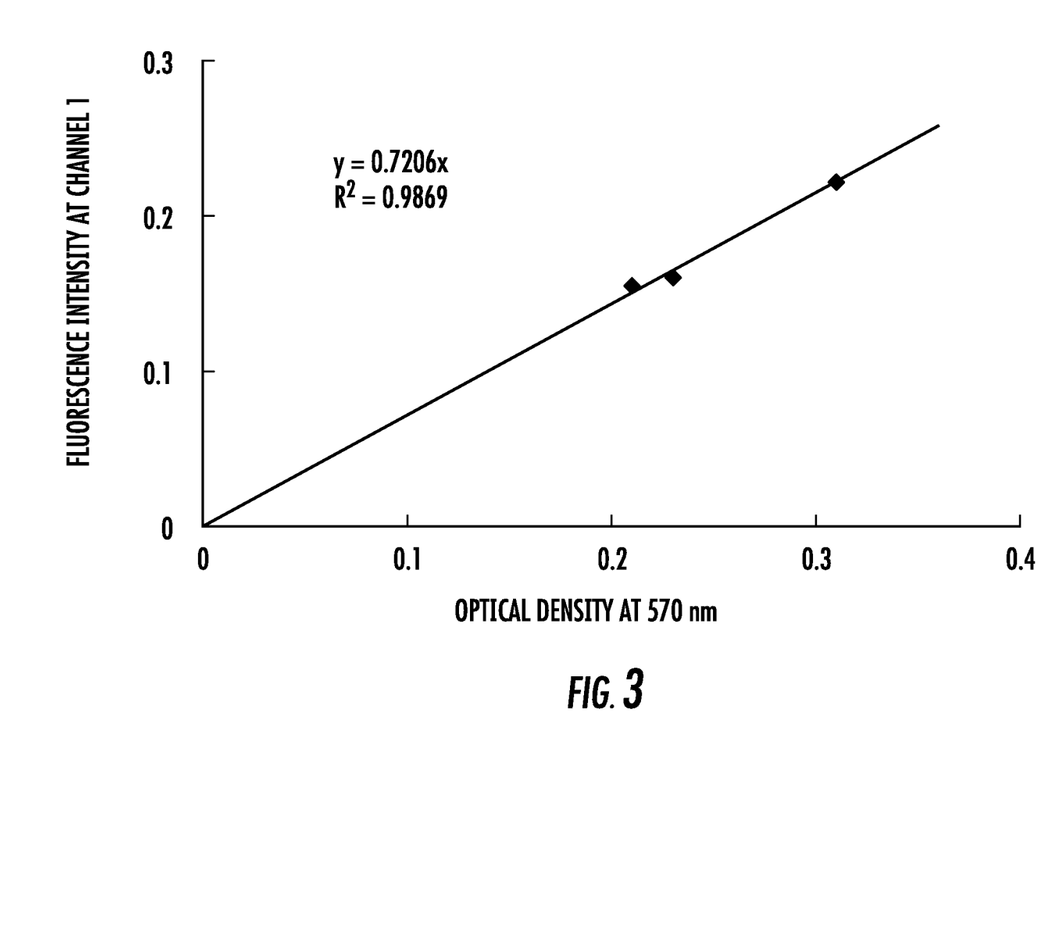
FIG. 3 is a graph showing a linear relationship in the comparison of fluorescence and color for light oil that demonstrates fluorescence may be interpreted as a measure of heavy end content in the oil.

FIG. 3 is a graph that compares the fluorescence with the color for light oil that still has measurable color. This figure shows on the vertical axis the fluorescence intensity at channel 1 and on the horizontal axis the optical density at 570 nanometers (nm). The linear relationship between the fluorescence and the color demonstrates that fluorescence can be interpreted as a relative measure of heavy end content in this oil. For oils that are even lighter, the measurement of color by absorption is not robust (very little of the incident light is absorbed, so a small absorption signal is measured on top of a large transmission background), while fluorescence is more robust (the fluorescence signal may be small, but it is measured on top of a very small background). This makes fluorescence appropriate for measuring heavy end content is gas condensates.

As noted above, the model compensational grading of heavy ends in the gas condensate reservoir is processed according to the FHZ EOS. Further details as an example of FHZ EOS are explained below. The compositional grading in the familiar black oils results from contrasts in density and solubility between the heavy ends as the asphaltenes and the rest of the oil as described by the FHZ EOS. The heavy ends and gas condensates such as the aromatics and resins similarly have contrasts in density and solubility from the rest of the condensate. Therefore, the heavy ends and gas condensates exhibit the compositional grading as described by the FHZ EOS. Heavy ends, black oils and mobile heavy oils have the asphaltene molecules, asphaltene nanoaggregates and/or asphaltene clusters. These particles have sizes of at least 1.5 nanometers (nm) as measured by laboratory standards and confirmed by the FHZ EOS analysis of the reservoir compositional gradients. The heavy ends and gas condensates such as the aromatics and resins are smaller molecules that do not form aggregates. They are expected to have particle sizes around 1 nm. For example, it has been found in one case that fluorescence in a particular light oil results primarily from a single compound called perylene, which has the size of around 1 nm and is expected to be representative of fluorophores in gas condensates. It should be understood that perylene analysis is an example that can be used in accordance with a non-limiting example.

Figure 4:
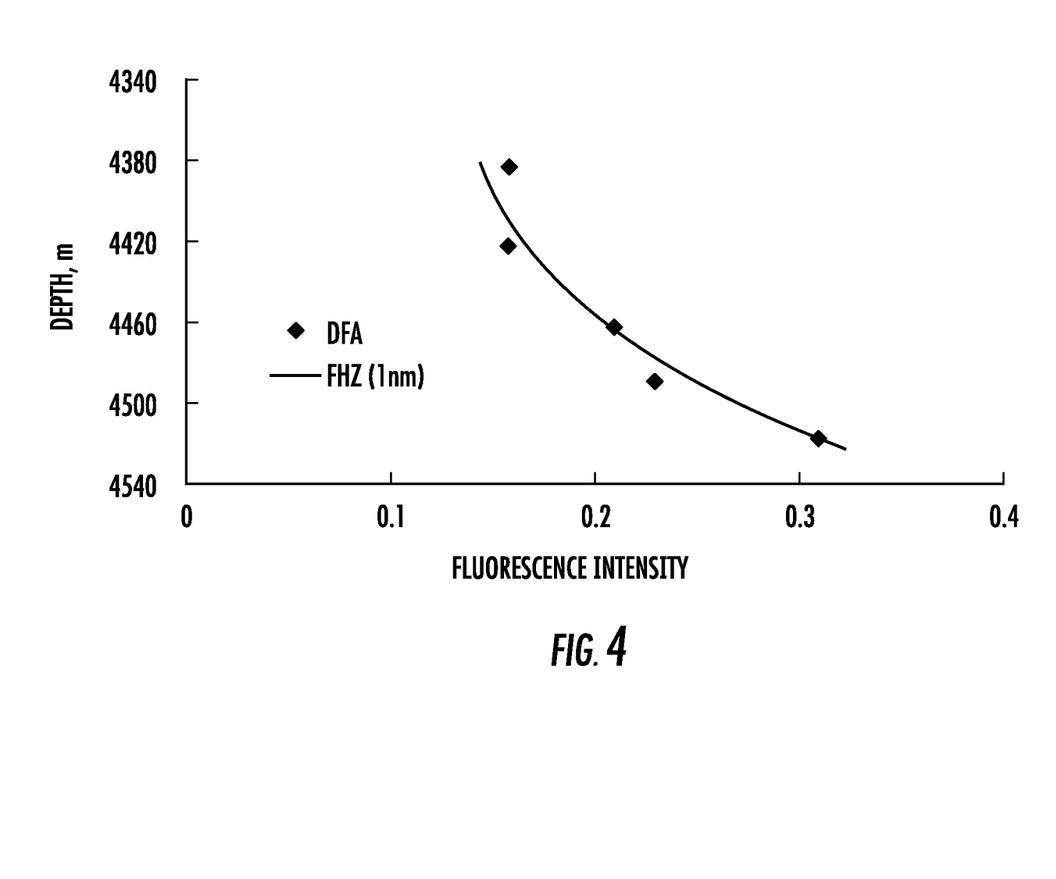
FIG. 4 is a graph showing fluorescence data measured at different depths with DFA and the straight line indicating the prediction from the FHZ EOS indicating that the reservoir is connected and at equilibrium.

As described above, the compositional gradients predicted by the FHZ EOS with about 1 nm particle size are compared with the fluorescence from different depths as measured by the DFA. An agreement between the prediction and measurement validates the assumptions of the FHZ EOS, showing equilibrium for a connected reservoir.

FIG. 4 shows a graph with the depth in meters on a vertical axis and the fluorescence intensity on the horizontal axis as an example of the workflow. The diamond points are fluorescence data measured at different depths with the DFA. The solid line is the prediction from the FHZ EOS. The good agreement shown in this graph suggests that this reservoir is connected and at equilibrium.

In the numerical model, the FHZ EOS simulates over time the equilibrium concentration of the heavy end gas condensates as a function of depth or location within the wellbore. The fluid samples are acquired from at least one wellbore and analyzed to measure the concentration and quantify the heavy end gas condensates. The simulated concentration as a function of location compared to the measured concentration as a function of location allows an analysis of the reservoir conductivity, which is used to determine where wellbores should be drilled and how the reservoir should be managed. In an example, the fluid reservoir within the wellbore is determined to be connected and in a state of equilibrium when differences between the simulated equilibrium concentration as a function of location within the wellbore and measured concentration such as of the heavy end gas condensates are below a threshold and compartmentalized when above the threshold.

The chemical composition of petroleum varies in different parts of a connected reservoir. This change in composition with position (e.g., depth) in the reservoir is referred to as compositional grading. The magnitude of this compositional grading (i.e., the difference in the composition of two fluids collected from different depthscan be measured with downhole fluid analysis (DFA) and predicted with the mathematical equation of state (EOS) model. The EOS model is based on assumptions that the reservoir is connected and at thermodynamic equilibrium. If the magnitude of compositional grading as measured matches the predicted composition grading, then the assumptions of the EOS model are confirmed. In the event that the magnitude of the measured compositional grading does not match the predictions of the EOS model, it can be assumed that there is reservoir compartmentalization or that the reservoir fluids are not in equilibrium. Many different forces can contribute to a lack of thermodynamic equilibrium, such as tar mats, water washing, biodegradation, and real-time charging. The methodology as described helps determine whether the reservoir is compartmentalized or in a state of thermodynamic non-equilibrium, to help in development decisions.

The equation of state (EOS) model describes the thermodynamic behavior of the fluid and provides for characterization of the reservoir fluid at different locations within the reservoir. With the reservoir fluid characterized with respect to its thermodynamic behavior, fluid production parameters, transport properties, and other commercially useful indicators of the reservoir can be computed.

The modeling step described above uses the Flory-Huggins-Zuo (FHZ) EOS model, that derives compositional gradients and other property gradients (e.g., pressure and temperature gradients) and describes the volumetric behavior of the oil and gas (and possibly water) mixture in reservoir fluids as a function of depth in the reservoir of interest. The compositional gradients derived from the FHZ EOS model include mass fractions, mole fractions, molecular weights, and specific gravities for a set of psuedocomponents of the formation fluid. Such psuedocomponents include a heavy psuedocomponent representing asphaltenes in the formation fluid, a second distillate psuedocomponent that represents the non-asphaltene liquid fraction of the formation fluid, and a third light psuedocomponent that presents gases in the formation fluid. The psuedocomponents derived from the FHZ EOS model can also represent single carbon number (SCAN) components and other fractions or lumps of the formation fluid (such as a water fraction) as desired. The FHZ EOS model can predict composition gradients with depth that take into account the impacts of gravitational forces, chemical forces, thermal diffusion, etc. as taught in International Patent Application Publication WO 2011/007268. Other applications of the FHZ EOS have been described in U.S. Pat. Nos. 7,822,554 and 7,920,970, US Patent Application Publications 2009/0248310 and 2009/0312997, International Patent Application Publications WO 2009/138911 and WO 2011/030243, U.S. patent application Ser. No. 12/752,967, and International Patent Application PCT/IB2011/051740.

Connectivity can be indicated by moderately decreasing GOR values with depth, a continuous increase of asphaltene content as a function of depth, and/or a continuous increase of fluid density and/or fluid viscosity as a function of depth. On the other hand, compartmentalization and/or non-equilibrium can be indicated by discontinuous GOR (or if lower GOR is found higher in the column), discontinuous asphaltene content (or if higher asphaltene content is found higher in the column), and/or discontinuous fluid density and/or fluid viscosity (or if higher fluid density and/or fluid viscosity is found higher in the column).

The fluid property predictions of the EOS are based on the assumption that the reservoir fluids within the wellbore are connected and in a state of thermodynamic equilibrium. Thus, the fluid properties measured by downhole fluid analysis can be accessed to confirm that they correspond to this expected architecture. More specifically, a likelihood that the reservoir is connected and in a state of equilibrium can be indicated by moderately decreasing GOR values with depth, a continuous increase of asphaltene content as a function of depth, and/or a continuous increase of fluid density and/or fluid viscosity as a function of depth. Moreover, a likelihood that the reservoir is connected and in a state of equilibrium can be indicated by consistencies (i.e., small differences) between the fluid property predictions of the EOS model (particularly GOR, asphaltene content, fluid density, and fluid viscosity) and the corresponding downhole fluid analysis measurements.

On the other hand, a likelihood that the reservoir is compartmentalized and/or in a state of non-equilibrium can be indicated by discontinuous GOR (or if lower GOR is found higher in the column), discontinuous asphaltene content (or if higher asphaltene content is found higher in the column), and/or discontinuous fluid density and/or fluid viscosity (or if higher fluid density and/or fluid viscosity is found higher in the column). A likelihood that the reservoir is compartmentalized and/or in a state of non-equilibrium can be indicated by inconsistencies (i.e., large differences) between the fluid property predictions of the EOS (particularly GOR, asphaltene content, fluid density, and fluid viscosity) and the corresponding downhole fluid analysis measurements.

The measurements of the hydrocarbon composition of fluid samples are derived by translation of the data output of a fluid analyzer. In the preferred embodiment, such translation employs an empirical relation that relates fluorescence to a measurement of concentration of a high molecular weight fraction of the reservoir fluids of the form:

$$I_F = C1 * \phi_a + C2, \quad (1)$$

where $I_F$ is the measured fluorescence of the formation fluid;
$\phi_a$ is the corresponding volume fraction of the high molecular weight fraction; and
C1 and C2 are constants derived from empirical data.

The GOR is determined by measuring the quantity of methane and liquid components of crude oil using near infrared absorption peaks. The ratio of the methane peak to the oil peak on a single phase live crude oil is directly related to GOR.

In the preferred embodiment, the solubility model treats the reservoir fluid as a mixture of two parts: a solute part (the high molecular weight fraction) and the oil mixture (or bulk reservoir fluid that includes the lower molecular weight fractions as well as the high molecular weight fraction). The properties of the oil mixture can be measured by downhole fluid analysis and/or estimated by an EOS model. It is assumed that the reservoir fluids are connected (i.e., there is a lack of compartmentalization) and in thermodynamic equilibrium. In this approach, the relative concentration (volume fraction) of the solute part as a function of depth is given by:

$$\frac{\phi_a(h_2)}{\phi_a(h_1)} = \exp\left\{ \frac{v_a g(\rho_m - \rho_a)(h_2 - h_1)}{RT} + \left(\frac{v_a}{v_m}\right)_{h_2} - \left(\frac{v_a}{v_m}\right)_{h_1} - \frac{v_a\left[(\delta_a - \delta_m)^2_{h_2} - (\delta_a - \delta_m)^2_{h_1}\right]}{RT} \right\} \quad (2)$$

where $\Phi_a(h_1)$ is the volume fraction for the solute part at depth $h_1$,
$\phi_a(h_2)$ is the volume fraction for the solute part at depth $h_2$,
$v_a$ is the partial molar volume for the solute part,
$v_m$ is the molar volume for the oil mixture,
$\delta_a$ is the solubility parameter for the solute part,
$\delta_m$ is the solubility parameter for the oil mixture,
$\rho_a$ is the partial density for the solute part,
$\rho_m$ is the density for the oil mixture,
R is the universal gas constant, and
T is the absolute temperature of the reservoir fluid.

In Eq. (2) it is assumed that properties of the solute part (e.g., the high molecular weight fraction) are independent of depth. For properties of the oil mixture that are a function of depth, average values between depths can be used. The first exponential term of Eq. (2) arises from gravitational contributions. The second and third exponential terms arise from the combinatorial entropy change of mixing. The fourth exponential term rises from the enthalpy (solubility) change of mixing. It can be assumed that the reservoir fluid is isothermal. In this case, the temperature T can be set to the average formation temperature as determined from downhole fluid analysis. Alternatively, a temperature gradient with depth (preferably a linear temperature distribution) can be derived from downhole fluid analysis and the temperature T at a particular depth determined from such temperature gradient.

The density $\rho_m$ of the oil mixture at one or more depths can be measured by downhole fluid analysis (or laboratory analysis of the reservoir fluids collected from a given depth at reservoir conditions). It can also be derived from the output of the EOS model.

The molar volume $v_m$ for the oil mixture at a given depth can be provided by the solution of EOS model or other suitable approach.

The solubility parameter $\delta_m$ for the oil mixture at a given depth can be derived from an empirical correlation to the density $\rho_m$ of the oil mixture at the given depth. For example, the solubility parameter $\delta_m$ (in $(MPa)^{0.5}$) can be derived from:

$$\delta_m = 17.347 \rho_m + 2.904 \quad (3)$$

where $\rho_m$ is the density of the oil mixture at the given depth in $g/cm^3$.

A linear function of the form of Eq. (4) can be used to correlate a property of the oil mixture (such as density $\rho_m$, molar volume $v_m$, the solubility parameter $\delta_m$, viscosity, etc.) as a function of depth by:

$$\alpha = c\Delta h + \alpha_{ref} \quad (4)$$

Where $\alpha$ is the property (such as density $\rho_m$, molar volume $v_m$, and the solubility parameter $\delta_m$) of the oil mixture,
c is a coefficient,
$\alpha_{ref}$ is the property of the oil mixture at a reference depth, and
$\Delta h$ is the difference in height relative to the reference depth.

The solubility parameter $\delta_a$ (in $MPa^{0.5}$) of the solute part at a given depth can be derived from the temperature gradient relative to a reference measurement station by:

$$\delta_a(T) = \delta_a(T_0)[1 - 1.07 \times 10^{-3}(\Delta T)] \quad (5)$$

where $T_0$ is the temperature at reference measurement station (e.g., $T_0 = 298.15$ K),
T is the temperature at the given depth,
$\Delta T = T - T_0$, and
$\delta_a(T_0)$ is a solubility parameter (in $MPa^{0.5}$) for the solute part at $T_0$ (e.g., $\delta_a(T_0) = 21.85$ $MPa^{0.5}$).

The impact of pressure on the solubility parameter for the solute part is small and negligible. The temperature gradient in the wellbore can be measured by an optical fiber distributed temperature sensor. Alternatively, the temperature in the wellbore can be measured by downhole fluid analysis at multiple stations. A linear function of the form of Eq. (4) can be used to derive the temperature gradient between stations as a function of depth.

Both temperature and pressure can be accounted for in determining the solubility parameter $\delta_a(P,T)$ for the solute part as:

$$\delta_a(P, T) = \delta_a(P_0, T)\left(\frac{v}{v_0}\right)_T^{-1.25} \quad (6)$$

where P, v, and $P_0$ are the pressure, molar volume and the reference pressure, respectively, which can be measured or estimated from the output of the EOS.

The partial density (in $kg/m^3$) of the solute part can be derived from a constant that can vary for the different solute part classes, such as 1.05 $kg/m^3$ for resins, 1.15 $kg/m^3$ for asphaltene nanoaggregates, and 1.2 for asphaltene clusters.

Once the properties noted above are obtained, the remaining adjustable parameter in Eq. (2) is the molar volume of the solute part. The molar volume of the solute part varies for different classes of the high molecular weight fraction. For example, resins have a smaller molar volume than asphaltene nanoaggregates, which have a smaller molar volume than asphaltene clusters. The model assumes that the molar volume of the solute part is constant as function of depth. A spherical model is preferably used to estimate the molar volume of the solute part by:

$$V = \frac{1}{6} * \pi * d^3 * Na \quad (7)$$

where V is the molar volume, d is the molecular diameter, and Na is Avogadro's constant.

For example, for the class where the solute part includes resins (with little or no asphaltene nanoaggregates and asphaltene clusters), the molecular diameter d can vary over a range of 1.25±0.15 nm. For the class where the solute part includes asphaltene nanoaggregates (with little or no resins and asphaltene clusters), the molecular diameter d can vary over a range of 1.8±0.2 nm. For the class where the solute part includes asphaltene clusters (with little or no resins and asphaltene nanoaggregates), the molecular diameter d can vary over a range of 4.0±0.5 nm. For the class where the solute part is a mixture of resins and asphaltene nanoaggregates (with little or no asphaltene clusters), the molecular diameter d can vary over the range corresponding to such resins and nanoaggregates (e.g., between 1.25 nm and 1.8 nm). These diameters are exemplary in nature and can be adjusted as desired.

In this manner, Eq. (1) can be used to determine a family of curves for one or more solute part classes. For example, the solute part classes can include resins, asphaltene nanoaggregates, asphaltene clusters and combinations thereof. One solute part class can include resins with little or no asphaltene nanoaggregates or cluster. Another solute part class can include resins and asphaltene nanoaggregates with little or no clusters. A further solute part class can include asphaltene clusters with little or no resins and asphaltene nanoaggregates. The family of curves represents an estimation of the concentration of the solute part class as a function of height. Each curve of the respective family is derived from a molecular diameter d that falls within the range of diameters for the corresponding solute part class. A solution can be solved by fitting the curves to corresponding measurements of the concentration of the respective solute part class at varying depths as derived from downhole fluid analysis to determine the best matching curve. For example, the family of curves for the solute part class including resins (with little or no asphaltene nanoaggregates and clusters) can be fit to measurements of resin concentrations at varying depth. In another example, the family of curves for the solute part class including asphaltene nanoaggregates (with little or no resins and asphaltene clusters) can be fit to measurements of asphaltene nanoaggregate concentrations at varying depth.

In yet another example, the family of curves for the solute part class including resins and asphaltene nanoaggregates (with little or no asphaltene clusters) can be fit to measurements of mixed resins and asphaltene nanoaggregate concentrations at varying depth. In still another example, the family of curves for the solute part class including asphaltene clusters (with little or no resins and asphaltene nanoaggregates) can be fit to measurements of asphaltene cluster concentrations at varying depth. If a best fit is identified, the estimated and/or measured properties of the best matching solute class (or other suitable properties) can be used for reservoir analysis. If no fit is possible, then the reservoir fluids might not be in equilibrium or a more complex formulism may be required to describe the petroleum fluid in the reservoir.

Other suitable structural models can be used to estimate and vary the molar volume for the different solute part classes. It is also possible that Eq. (2) can be simplified by ignoring the first and second exponent terms, which gives an analytical model of the form:

$$\frac{\phi_a(h_2)}{\phi_a(h_1)} = \exp\left\{\frac{v_i g(\rho_m - \rho_a)(h_2 - h_1)}{RT}\right\} \quad (8)$$

This Eq. (8) can be solved in a manner similar to that described above for Eq. (2) in order to derive the relative concentration of solute part as a function of depth (h) in the reservoir.

An illustrative example of an FHZ EOS model now follows and assumes that there are reservoir fluids with a number of compositional components and that the reservoir fluids are connected (i.e., there is a lack of compartmentalization) and in a state of thermodynamic equilibrium. Moreover, it is assumed that there are no adsorption phenomena or any kind of chemical reactions in the reservoir. The mass flux (J) of compositional component i that crosses the boundary of an elementary volume of the porous media is expressed as:

$$J_i = \rho_i \left( \sum_{j=1}^{n} (L_{ij} \nabla_T g_j^t) + L_{ip}(\rho g - \nabla P) + L_{iq} \nabla T \right) \quad (9)$$

where $L_{ij}$, $L_{ip}$, and $L_{iq}$ are the phenomenological coefficients,
$\rho_i$ denotes the partial density of component i,
$\rho$, g, P, T are the density, the gravitational acceleration, pressure, and temperature, respectively, and
$g_j^t$ is the contribution of component j to mass free energy of the fluid in a porous media, which can be divided into a chemical potential part $\mu_i$ and a gravitational part gz (where z is the vertical depth).

The average fluid velocity (u) is estimated by:

$$u = \frac{\sum_{j=1}^{n} J_j}{\rho}. \quad (10)$$

According to Darcy's law, the phenomenological baro-diffusion coefficients must meet the following constraint:

$$\frac{k}{\eta} = \frac{\sum_{j=1}^{n} \rho_j L_{jp}}{\rho} \quad (11)$$

where k and $\eta$ are the permeability and the viscosity, respectively.

If the pore size is far above the mean free path of molecules, the mobility of the components, due to an external pressure field, is very close to the overall mobility. The mass chemical potential is a function of mole fraction (x), pressure, and temperature.

At constant temperature, the derivative of the mass chemical potential (t) has two contributions:

$$\nabla_T \mu_j = \sum_{k=1}^{n} \left(\frac{\partial \mu_j}{\partial x_k}\right)_{T,P,x_{i \neq k}} \quad (12)$$

-continued $$\nabla x_k + \left(\frac{\partial \mu_j}{\partial P}\right)_{T,x} \nabla P$$

where the partial derivatives can be expressed in terms of EOS (fugacity coefficients):

$$\left(\frac{\partial \mu_j}{\partial x_k}\right)_{T,P,x_{j\neq k}} = \frac{RT}{M_j}\left(\frac{\partial \ln f_j}{\partial x_k}\right)_{T,P,x_{j\neq k}} \quad (13)$$

$$= \frac{RT}{M_j}\left(\frac{\delta_{jk}}{x_k} + \frac{1}{\varphi_j}\left(\frac{\partial \varphi_j}{\partial x_k}\right)_{T,P,x_{j\neq k}}\right)$$

$$\left(\frac{\partial \mu_j}{\partial P}\right)_{T,x} = \frac{\bar{v}_j}{M_j} = \frac{RT}{M_j}\left(\frac{1}{P} + \left(\frac{\partial \varphi_j}{\partial P}\right)_{T,x}\right) \quad (14)$$

where $M_j$, $f_j$, $\phi_j$, and $v_j$ are the molecular weight, fugacity, fugacity coefficient, and partial molar volume of component j, respectively;

$x_k$ is the mole fraction of component k;
R denotes the universal gas constant; and
$\delta$ is the Kronecker delta function.

In the ideal case, the phenomenological coefficients (L) can be related to effective practical diffusion coefficients ($D_i^{eff}$):

$$L_{ii} = -\frac{M_i}{RT}D_i^{eff}. \quad (15)$$

The mass conservation for component i in the reservoir fluid, which governs the distribution of the components in the porous media, is expressed as:

$$\frac{\partial \rho_i}{\partial t} + \nabla J_i = 0, i = 1, 2, \cdots, n. \quad (16)$$

Eq. (16) can be used to solve a wide range of problems. This is a dynamic model which is changing with time t.

Consider that the mechanical equilibrium of the fluid column has been achieved:

$$\nabla_z P = \rho g. \quad (17)$$

The vertical distribution of the components can be calculated by solving the following set of equations:

$$\frac{\partial \ln f_i}{\partial z} - \frac{M_i g}{RT} + \frac{J_{i,z}}{x_i D_i^{eff}}\frac{M}{\rho M_i} - \frac{L_{iq}}{D_i^{eff}}\frac{\partial T}{\partial z} = 0, i = 1, 2, \cdots, n \text{ and} \quad (18)$$

$$\sum_{k=1}^{n}\left(\frac{\delta_{ik}}{x_k} + \frac{1}{\varphi_i}\frac{\partial \varphi_i}{\partial x_k}\right)\nabla_z x_k + \frac{(v_i\rho - M_i)g}{RT} + \frac{J_{i,z}}{x_i D_i^{eff}}\frac{M}{\rho M_i} - \frac{L_{iq}}{D_i^{eff}}\frac{\partial T}{\partial z} = 0 \quad (19)$$

where $J_{i,z}$ is the vertical component of the external mass flux. This formulation allows computation of the stationary state of the fluid column and it does not require modeling of the dynamic process leading to the observed compositional distribution.

If the horizontal components of external fluxes are significant, the equations along the other axis have to be solved as well. Along a horizontal "x" axis the equations become:

$$\frac{\partial \ln f_i}{\partial x} + \frac{J_{i,x}}{x_i D_i^{eff}}\frac{M}{\rho M_i} - \frac{L_{iq}}{D_i^{eff}}\frac{\partial T}{\partial x} = 0. \quad (20)$$

The mechanical equilibrium of the fluid column $\nabla_z P = \rho g$, is a particular situation which will occur only in highly permeable reservoirs. In the general case, the vertical pressure gradient is calculated by:

$$\nabla_z P = \rho g - \frac{\nabla_z P_{Fluxes} + \nabla_z P_{Soret}}{1 + R_p} \quad (21)$$

where $R_p$ is calculated by:

$$R_p = RT\frac{k}{\eta}\frac{\rho}{M}\sum_{i=1}^{n}\frac{x_i}{D_i^{eff}}. \quad (22)$$

The pressure gradient contribution from thermal diffusion (so-called Soret contribution) is given by:

$$\nabla_z P_{Soret} = RT\frac{\rho}{M}\sum_{i=1}^{n}x_i\frac{L_{iq}}{D_i^{eff}}\nabla_z T. \quad (23)$$

And the pressure gradient contribution from external fluxes is expressed as $$\nabla_z P_{Fluxes} = RT\sum_{i=1}^{n}\frac{J_{i,z}}{M_i D_i^{eff}}. \quad (24)$$

Assuming an isothermal reservoir and ignoring the external flux, results in the following equation:

$$\frac{\partial \ln f_i}{\partial z} - \frac{M_i g}{RT} = 0, i = 1, 2, \cdots, n. \quad (25)$$

Eq. (25) can be rewritten as:

$$\frac{\partial \ln f_i}{\partial z} - \frac{M_i g}{RT} + a_i = 0, i = 1, 2, \cdots, n \quad (26)$$

where $a_i$ is computed by:

$$a_i = \frac{J_{i,z}}{x_i D_i^{eff}}\frac{M}{\rho M_i} - \frac{L_{iq}}{D_i^{eff}}\frac{\partial T}{\partial z}, i = 1, 2, \cdots, n. \quad (27)$$

Eq. (26) and (27) can be solved to predict compositions and volumetric behavior of oil and gas mixtures in the reservoir. Flash calculations are used to solve for the fugacities ($f_i$) of the components of the oil and gas mixtures in equilibrium.

Many modifications and other embodiments of the invention will come to the mind of one skilled in the art having the benefit of the teachings presented in the foregoing descrip- That which is claimed is:

1. A method of assessing connectivity between sections in a hydrocarbon reservoir, comprising:
   collecting a plurality of hydrocarbon samples over corresponding different depths within the hydrocarbon reservoir;
   using fluorescence intensity to determine a plurality of actual heavy end concentrations of hydrocarbons for the corresponding different depths based upon the plurality of hydrocarbon samples;
   determining a plurality of estimated heavy end concentrations of hydrocarbons for the corresponding different depths; and
   comparing the plurality of actual heavy end concentrations of hydrocarbons with the plurality of estimated heavy end concentrations of hydrocarbons to assess connectivity between sections of the hydrocarbon reservoir.

2. The method according to claim 1 wherein the hydrocarbon comprises a gas condensate.

3. The method according to claim 1 wherein the hydrocarbon comprises a wet gas.

4. The method according to claim 1 wherein the hydrocarbon comprises a volatile oil.

5. The method according to claim 1 wherein the hydrocarbon comprises a fluid containing <1 wt % asphaltene.

6. The method according to claim 1 wherein the hydrocarbon comprises fluid with <0.1 optical density(OD) absorption in the visible or near-infrared spectral regions.

7. The method according to claim 1 wherein the hydrocarbon comprises fluid having heavy ends exist as isolated molecules.

8. The method according to claim 1 wherein the hydrocarbon comprises fluid having fluorescence that is proportional to the heavy end content.

9. The method according to claim 1 wherein the plurality of estimated heavy end concentrations of hydrocarbons have a gradient over the depth of a wellbore indicative of connectivity between sections of the hydrocarbon reservoir.

10. The method according to claim 1 wherein determining the plurality of estimated heavy end concentrations comprises using a Flory-Huggins-Zuo Equation of State (FHZ EOS) model.

11. A system of assessing connectivity between sections in a hydrocarbon reservoir traversed by at least one wellbore, the system comprising:
   at least one tool to
      collect a plurality of hydrocarbon samples over corresponding different depths within the at least one wellbore, and
      use fluorescence intensity to determine a plurality of actual heavy end concentrations of hydrocarbons for the corresponding different depths based upon the plurality of hydrocarbon samples; and
   a processor cooperating with said at least one tool to
      determine a plurality of estimated heavy end concentrations of hydrocarbons for the corresponding different depths, and
      compare the plurality of actual heavy end concentrations of hydrocarbons with the plurality of estimated heavy end concentrations of hydrocarbons to assess connectivity between sections of the hydrocarbon reservoir.

12. The system according to claim 11 wherein the plurality of estimated heavy end concentrations have a gradient over the depth of the wellbore indicative of connectivity between sections of the hydrocarbon reservoir.

13. The system according to claim 11 wherein said processor determines the plurality of estimated heavy end concentrations using a Flory-Huggins-Zuo Equation of State (FHZ EOS) model.

14. The system according to claim 11 wherein the heavy end concentrations are based upon concentrations of aromatics and resins.

15. A non-transitory computer readable medium executable on a processor to perform steps to assess connectivity between sections in a hydrocarbon reservoir traversed by at least one wellbore from which a plurality of hydrocarbon samples have been collected over corresponding different depths within the wellbore, and for which fluorescence intensity has been used to determine a plurality of actual heavy end concentrations of hydrocarbons for the corresponding different depths based upon the plurality of hydrocarbon samples, the steps comprising:
   determining a plurality of estimated heavy end concentrations of hydrocarbons for the corresponding different depths; and
   comparing the plurality of actual heavy end concentrations of hydrocarbons with the plurality of estimated heavy end concentrations of hydrocarbons to assess connectivity between sections of the hydrocarbon reservoir.

16. The non-transitory computer readable medium according to claim 15 wherein the plurality of estimated heavy end concentrations have a gradient over the depth of the wellbore indicative of connectivity between sections of the hydrocarbon reservoir.

17. The non-transitory computer readable medium according to claim 15 wherein determining the plurality of estimated heavy end concentrations comprises using a Flory-Huggins-Zuo Equation of State (FHZ EOS) model.

18. The non-transitory computer readable medium according to claim 15 wherein the heavy end concentrations are based upon concentrations of aromatics and resins.

* * * * *